United States Patent [19]
O'Keefe et al.

[11] Patent Number: 6,010,711
[45] Date of Patent: *Jan. 4, 2000

[54] METHODS, ARTICLES AND COMPOSITIONS FOR THE PHARMACOLOGIC INHIBITION OF BONE RESORPTION WITH PHOSPHODIESTERASE INHIBITORS

[75] Inventors: Regis James O'Keefe; Randy Nathan Rosier, both of Pittsford, N.Y.

[73] Assignee: University of Rochester, Rochester, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/592,123

[22] Filed: Jan. 26, 1996

[51] Int. Cl.$^7$ .................................. A61F 2/28; A61F 2/00
[52] U.S. Cl. ..................... 424/423; 514/233.2; 514/82; 514/263; 424/422
[58] Field of Search ................. 424/423; 514/233.2, 514/82, 263

[56] References Cited

U.S. PATENT DOCUMENTS

| | | | |
|---|---|---|---|
| 5,118,500 | 6/1992 | Hanel et al. | 424/85.1 |
| 5,215,459 | 6/1993 | Ney et al. | 433/215 |
| 5,272,153 | 12/1993 | Mandell et al. | 514/263 |
| 5,281,419 | 1/1994 | Tuan et al. | 424/426 |
| 5,498,422 | 3/1996 | Nakamichi et al. | 424/451 |
| 5,591,776 | 1/1997 | Cavalla et al. | 514/622 |
| 5,603,954 | 2/1997 | Wong et al. | 424/473 |
| 5,648,389 | 7/1997 | Gans et al. | 514/557 |
| 5,681,873 | 10/1997 | Norton et al. | 523/115 |

FOREIGN PATENT DOCUMENTS 3543164  6/1997  Germany.

OTHER PUBLICATIONS

Chiba, Junji, M.D. et al., 1994 "The Characterization of Cytokines in the Interface Tissue Obtained From Failed Cementless Total Hip Arthroplasty With and Without Femoral Osteolysis" Clinical Orthopadeics and Related Research 300:304–311.

Jiranek, William A., M.D. et al., 1993 "Production of Cytokines around Loosened Cemented Acetabular Components" The Journal of Bone and Joint Surgery. Incorporated vol. 75–A, No. 6 pp. 863–879.

Saffer, et al., "Interleukin–1 production by activated macrophages surrounding loosened orthopaedic implants: a potential role in osteolysis", *Br. J. Rheumatology*, 33, 309–316 (1994).

Bertolini et al., "Stimulation of bone resorption and inhibition of bone formation in vitro by human tumour necrosis factors", *Nature*, 319, 516–518 (1986).

Galvin et al., "Development and characterization of a porcine model to study osteoclast differentiation and activity", *Bone*, 19, 271–279 (1996).

Glant et al., "Response of three murine macrophage populations to particulate debris: bone resorption in organ cultures", *J. Orthop. Res.*, 12, 720–731 (1994).

Goldring et al., "The synovial–like membrane at the bone–cement interface in loose total hip replacements and its proposed role in bone lysis", *J. Bone & Joint Surg.*, 65A, 575–583 (1983).

Howie et al., "The response to particuate debris", *Ortho. Clin. North Amer.*, 24, 571–581 (1993).

Howie et al., "A rat model of resorption of bone at the cement–bone interface in the presence of polyethylene wear particles", *J. Bone & Joint Surg.*, 70A, 257–263 (1988).

Horowitz et al., "Studies of the mechanism by which the mechanical failure of polymethylmethacrylate leads to bone resorption", *J. Bone & Joint Surg.*, 75A, 802–813 (1993).

Kadoya et al., "Direct bone resorption by macrophages and their polykaryons in failed total joint arthroplasty", *J. Bone Miner. Res.*, 9, 309 (1994).

Macon et al., "Interleukin–4 may contribute to the abundant T–cell reaction and paucity of neoplastic B cells in T–cell– Rich–B–cell lymphomas", *Amer. J. Path.*, 141, 1031–1036 (1992).

Margevicius et al., "Isolation and Characterization of Debris in Membranes Around Total Joint Prostheses", *J. Bone & Joint Surg.*, 76A, 1664–1675 (1994).

Merkel et al., "Deletion of the P55 and P75 tumor necrosis factor receptors prevents implant osteolysis", *J. Bone Min. Res.*, 12, S441 (1997).

Merkel et al., "The role of TNF in particle–induced osteolysis in–vitro and in–vivo", *Orthop. Res. Soc.*, 22, 742 (1997).

Miossec et al., "Inhibition of the production of proinflammatory cytokines and immunoglobulins by interleukin–4 in an ex vivo model of rheumatoid synovitis", *Arthritis & Rheum.*, 35, 874–883 (1992).

Neuner et al., "Pentoxifylline in vivo down–regulates the release of IL–1β, IL–6, IL–8, and tumour necrosis factor–alpha by human peripheral blood mononuclear cells", *Immunology*, 83, 262–267 (1994).

(List continued on next page.)

*Primary Examiner*—Chris Eisenschenk
*Assistant Examiner*—Mary K. Zeman
*Attorney, Agent, or Firm*—Webb Ziesenheim Logsdon Orkin & Hanson, P.C.

[57] ABSTRACT

A class of active agents, and articles and compositions containing them and methods for treating human patients with them, which inhibit bone resorption of all types. This class of active agents comprises phosphodiester inhibiting compositions which inhibit any of interleukin 1 (IL1), interleukin 6 (IL6) and tumor necrosis factor alpha (TNF), which are cytokines that mediate bone resorption. Exemplary compositions in this class include: pentoxifylline; isobutylmethyl xanthine; ciprofloxacin; rolipram; terferol; and the quinolones generally. Each of these IL1/IL6/TNF inhibitors may be administered alone or in combination by a variety of delivery routes and dosage forms, and they may optionally be administered in conjunction with additional active agents including but not limited to metal chelators.

8 Claims, 2 Drawing Sheets

OTHER PUBLICATIONS

Parry et al., "Synovial fluid IL–6 levels in failed total joint arthroplasty with osteolysis", *Orthop. Res. Soc.*, 216–236 (1995).

Puzas et al., "Regulation of osteoclastic activity in infection", *Methods Enzymol.*, 236, 47–58 (1994).

Ralston, "Analysis of gene expression in human bone biopsies by polymerase chain reaction: evidence for enhanced cytokine expression in postmenopausal osteoporosis", *J. Bone Miner. Res.*, 9, 883–890 (1994).

Ransjö et al., "Delayed stimulation of bone resorption in vitro by phosphodiesterase inhibitors requires the presence of adenylate cyclase stimulation", *Bone Min.*, 3, 225–234 (1988).

Suzuki et al., "Calcitonin–induced changes in the cytoskeleton are mediated by a signal pathway associated with protein kinase A in osteoclasts", *Endocrinology*, 137, 4685–4690 (1996).

Votta et al. Bon 15 (5) pp.533–538, Oct. 1, 1994.

Lerner et al. 1981 Acta Endocrinologica v 97 pp. 281–288, Jun. 1, 1981.

Lerner et al. 1986 Biochem Pharmacol. v 35 n 23 pp. 4177–4189, Dec. 1, 1986.

Ransjo et al. 1988 Bone and Mineral v 3 pp. 225–234, Jan. 1, 1988.

Seckinger et al. 1990 J Immunology 145 (12) pp. 4181–4184, Dec. 15, 1990.

Meffert et al. 1992 Z Antimikrob. Antineoplast. Chemother. 10 (1) 29–32, abstract only, Jan. 1992.

Gentschew et al. 1987 Fortschr. Antimikrob. Antineoplast. Chemother. 6 (1) 207–215 abstract only, Jan. 1987.

METHODS, ARTICLES AND COMPOSITIONS FOR THE PHARMACOLOGIC INHIBITION OF BONE RESORPTION WITH PHOSPHODIESTERASE INHIBITORS

FIELD OF THE INVENTION

The invention pertains to methods of administering active agents to inhibit unwanted bone resorption, and pharmaceutical compositions and articles containing such active agents.

BACKGROUND OF THE INVENTION

The unwanted loosening of orthopaedic implants of all types, including prosthodontic implants, is emerging as an enormous clinical problem in the United States and worldwide. In the United States alone, between 200,000 and 300,000 orthopaedic and prosthodontic implant procedures are performed annually, and it is anticipated that these numbers will continue to increase over time. It is estimated that after a service life of 10 or more years, approximately 10% of these implants will become loose due to periprosthetic bone resorption.

Unwanted bone loss also occurs in response to other conditions including but not limited to bone tumors and inflammatory arthritis. Clinical problems of various etiologies thus include not only the loosening of total joint arthroplasties and dental implants but also periarticular bone loss in inflammatory arthritis and pathologic fractures from carcinoma which is metastatic to bone or primary bone tumors such as Ewing's sarcoma or lymphoma (also generally known as round cell tumors). Bone resorption is thus a much more widespread affliction than may be evident from prosthesis-loosening statistics alone.

Surgical correction of undesirable bone resorption will never constitute an ideal treatment for bone loss, in part because surgery is generally the most invasive and traumatic solution to any medical condition and, more importantly, because it is only reactive and cannot be used preventively. The ideal solution to unwanted bone resorption would be a pharmacologically active approach wherein one or more active agents could be delivered to the area of bone resorption to halt and/or to prevent it. A need thus exists for a method of treating and/or preventing bone loss by means of methods and compositions for the pharmacologic inhibition of bone resorption.

BRIEF DESCRIPTION OF THE INVENTION

In order to meet this need, the present invention includes identification of a class of active agents, and compositions and articles containing them and methods for treating human patients with them, which inhibit bone resorption of all types. This class of active agents comprises phosphodiesterase inhibiting compositions which inhibit any of interleukin 1 (IL1), interleukin 6 (IL6) and tumor necrosis factor alpha (TNF), which are cytokines that mediate bone resorption. Exemplary compositions in this class include: pentoxifylline; isobutylmethylxanthine; ciprofloxacin; rolipram; terferol; and the quinolones generally. Each of these IL1/IL6/TNF inhibitors may be administered alone or in combination by a variety of delivery routes and dosage forms and optionally in conjunction with additional active agents including but not limited to metal chelators.

DETAILED DESCRIPTION OF THE INVENTION

Figure 1:
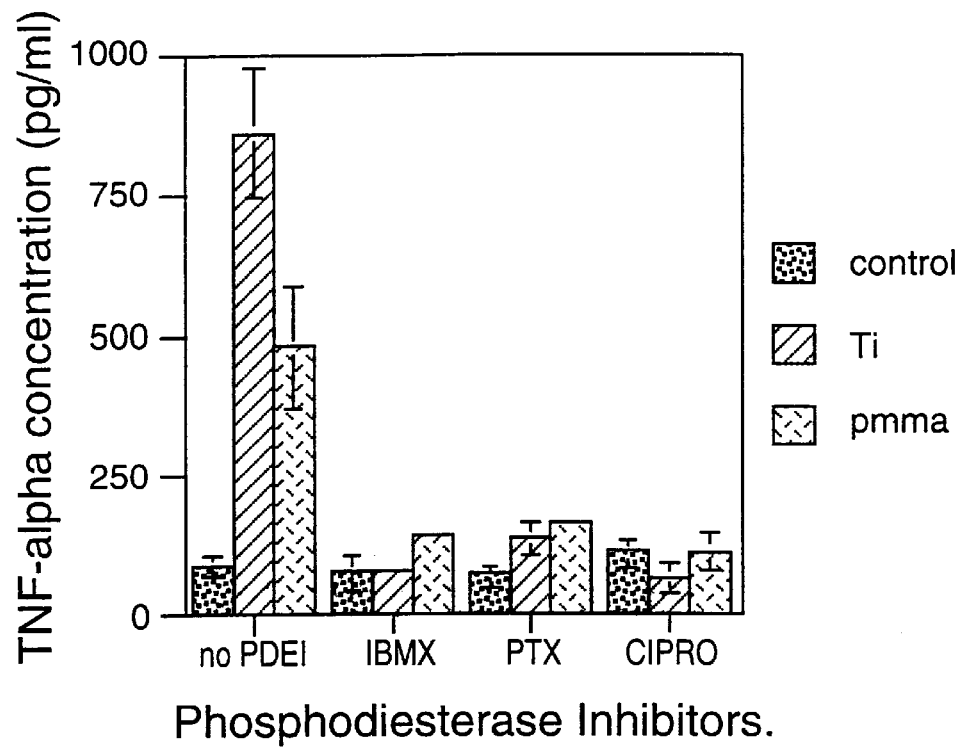
FIG. 1 is a bar graph illustrating the effect of phosphodiesterase inhibitors on TNF-α release by peripheral blood monocytes.

The present invention is predicated upon the discovery that not only are cytokines present in the area of bone resorption, surprisingly the pharmacologic inhibition of these cytokines with phosphodiesterase inhibitors can halt or prevent bone resorption. Previously, it was noted by others that when, for example, particulate debris incites an inflammatory response, the macrophages or monocytes which ingest the particulates increase their production of IL1, IL6 and TNF (see Jiranek, W. A., et al., "Production of cytokines around loosened cemented acetabular components/Analysis with immunohistochemical techniques and in situ hybridization," *J. Bone Joint Surg.*, vol. 75; A, pp. 863–879 (1993); see also Chiba, J, et al., "The characterization of cytokines in the interface tissue obtained from failed cementless total him arthroplasty with and without femoral osteolysis," *ClinOrthop*, vol. 300, pp. 204–312 (1994)). These and other investigators never taught or suggested, however, the pharmacologic suppression of cytokines as a means of prevention of bone resorption. Macrophages and monocytes were heretofore understood to be the direct agents of bone resorption, which theory was consistent with the usual mechanism of macrophage action, so any importance in the presence of the cytokines was generally never investigated. Now, however, as disclosed herein it has been discovered that the pharmacologic suppression of IL1, IL6 or TNF will in turn inhibit bone resorption, because the bone loss itself has been found to be cytokine-mediated. Thus, in direct contrast to the incorrect and misleading assumptions of those skilled in the art, the present invention administers active agents which inhibit the cytokines IL1, IL6 or TNF for the purpose of halting or preventing cytokine-mediated bone resorption. Furthermore, in destruction of bone by metastatic or primary bone tumors, which can lead to pathologic fractures, it was previously thought that the tumor cells themselves resorbed the bone by an unknown mechanism. However, the inventors have recently discovered the surprising phenomenon that the tumor cells involved in bone destruction secrete the same aforementioned bone resorption stimulating cytokines, IL1, IL6 and TNF. These cytokines in turn stimulate the bone resorbing cells, allowing the tumor locally to advance. Thus, pharmacologic inhibition of cytokines could be used to prevent pathologic fractures and tumor progression. These active agents may be administered by a wide variety of routes and dosage forms.

The cytokine-suppressing active agents according to the present invention include phosphodiesterase inhibitors such as pentoxifylline, isobutylmethylxanthine, ciprofloxacin, rolipram, terferol, and the quinolones generally. Each of these IL1/IL6/TNF inhibitors may be administered alone or in combination. Traditional oral, peroral, transdermal, transmucosal (sublingual, buccal, oral topical) and subcutaneous (injectable) dosage forms are encompassed by this disclosure, as well as dosage forms specifically tailored to deliver active agent to the site of actual or potential prosthetic loosening, such as for example active-agent containing bone cements or local implants or even sustained or delayed release active-agent containing or coated constructs for incorporation into or within prosthetic joints and implants themselves. In cases of tumors involving bone, systemic administration using intravenous, oral, transdermal, and other related methods, is generally indicated. While little is known at this writing of the mechanism of action which permits these active agents to halt or to prevent bone resorption, that they do can be confirmed experimentally.

The phosphodiesterase inhibitor active agents according to the present invention may be administered singly or in combination and optionally in conjunction with additional active agents including but not limited to metal chelator compounds and compositions. Such metal chelators include chemical genera such as hydroxamates and bisphosphonates; two specific metal chelators are diethyldithiocarbamate (DDTC) and tetracycline.

When one or more of the listed active agents is included in a bone cement, the active agents alone may be admixed into a cement such as the known methylmethacrylate bone cement in an amount between about 0.001–10% by weight of the weight of the cement. The active agent need not be admixed directly into a cement or its components, however, but may if desired be encapsulated in sustained- or controlled release hollow spheres or microspheres or other encapsulation means. Encapsulation of the active agent in the cement can prolong or delay the release of the active agent from the cement for applications where this result is desirable. For example, many incidences of prosthesis loosening do not occur until years after the prosthetic implant surgery, and it is sometimes thus desirable to postpone release of the cytokine-suppressing agent for a few months or years during which the need for such an agent is small. Polymer capsules whose polymers naturally degrade after a certain number of months or years are thus ideally suited to this embodiment of the invention.

When the active agent is intended to be released directly from a construct in or within an artificial prosthesis, the construct may be crafted to incorporate the active agent (in an amount of about 0.001–10% by weight of the weight of the construct) within a matrix having the desired sustained or delayed release properties. It is even possible to create a co-polymer of sorts by polymerizing prosthetic materials in the presence of the desired active agent so as to entrap the active agent within the polymeric molecular interstices. Those skilled in the arts of sustained and controlled release will readily adapt the desired constructs to incorporate the desired pharmaceutically active agent therein. The same is true for implant dosage forms, which may include the present active agents for localized controlled or sustained release in the area of potential prosthetic loosening.

Controlled or sustained release of the present active agents is by no means necessary, however. It is within the scope of the invention to suppress cytokine-mediated bone resorption by any dosage form or delivery route, including but not limited to oral tablets or intravenous administration or any other delivery method. The active agent may be coated on part or all of a prosthesis. A particularly useful application of the present invention is to prevent loosening of prosthodontic implants with the topical, transdermal, transmucosal or submucosal delivery or injection of topical oral solutions, sublingual or buccal tablets, or even toothpastes, beads for insertion in the gingival sulcus or various submucosal deformable or solid implants or injections. As long as the active agent is delivered into the area of the affected or potentially affected bone, so that it may locally suppress cytokine-mediated bone resorption there, such a method is embraced by the invention disclosed herein.

The preferred active agent according to the present invention is ciprofloxacin, a known and approved antibiotic heretofore unknown for its cytokine-suppressing pharmaceutical activity. Apart from its antibiotic character, it causes no other major and possibly unwanted medicinal effects and documented adverse reactions to it are minimal. (By contrast, pentoxifylline is a known vasodilator whose dosing thus must be carefully controlled within acceptable limits.) Most preferably, ciprofloxacin given systemically is administered by the oral or intravenous route in an amount adequate to achieve a serum concentration 60 minutes post-administration between 1.0 and 10.0 $\mu$g/ml. The oral dosage form may be a tablet containing ciprofloxacin hydrochloride and inactive ingredients including starch, microcrystalline cellulose, silicon dioxide, crospovidone, magnesium stearate, hydroxypropyl methylcellulose, titanium dioxide, polyethylene glycol and water. Intravenous preparations are generally prepared in infusion solution containing dextrose, lactic acid as a solubilizing agent and hydrochloric acid for pH adjustment. Appropriate provision for sustained release may be designed into the dosage form and in fact preferably should be, inasmuch as the prosthesis loosening is caused over time and thus treatment and prevention should be effected over time as well.

The above assertions have been documented in in vitro tests according to the following example.

EXAMPLE 1

Figure 2:
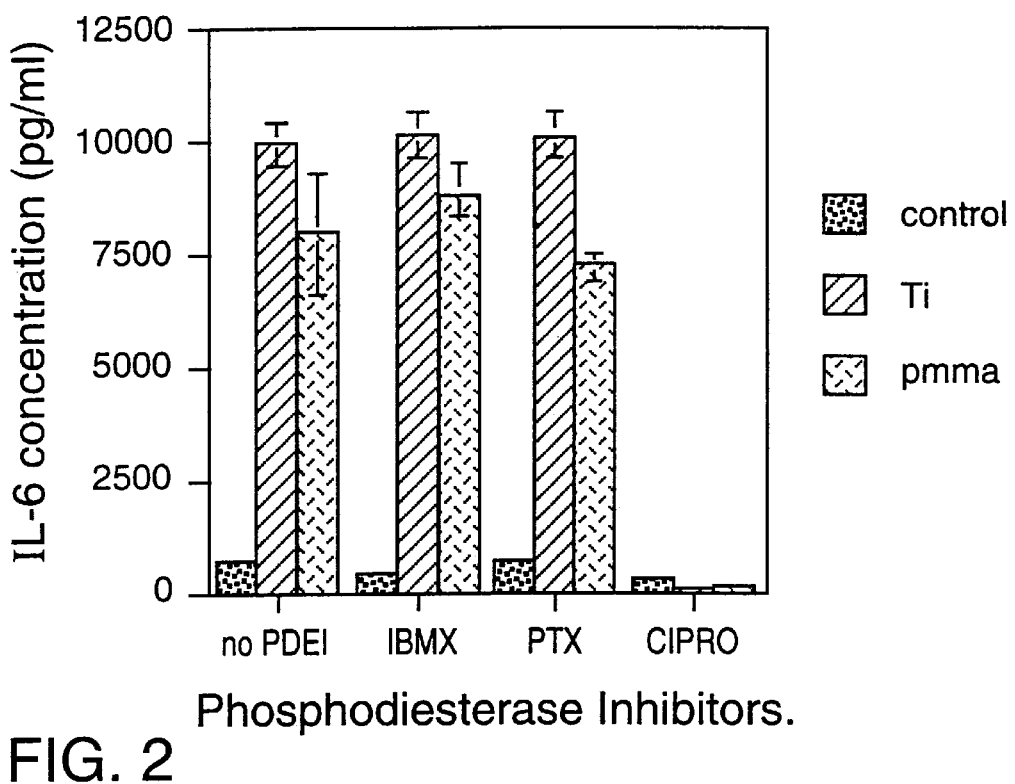
FIG. 2 is a bar graph illustrating the effect of phosphodiesterase inhibitors on IL-6 release by peripheral blood monocytes.
Figure 3:
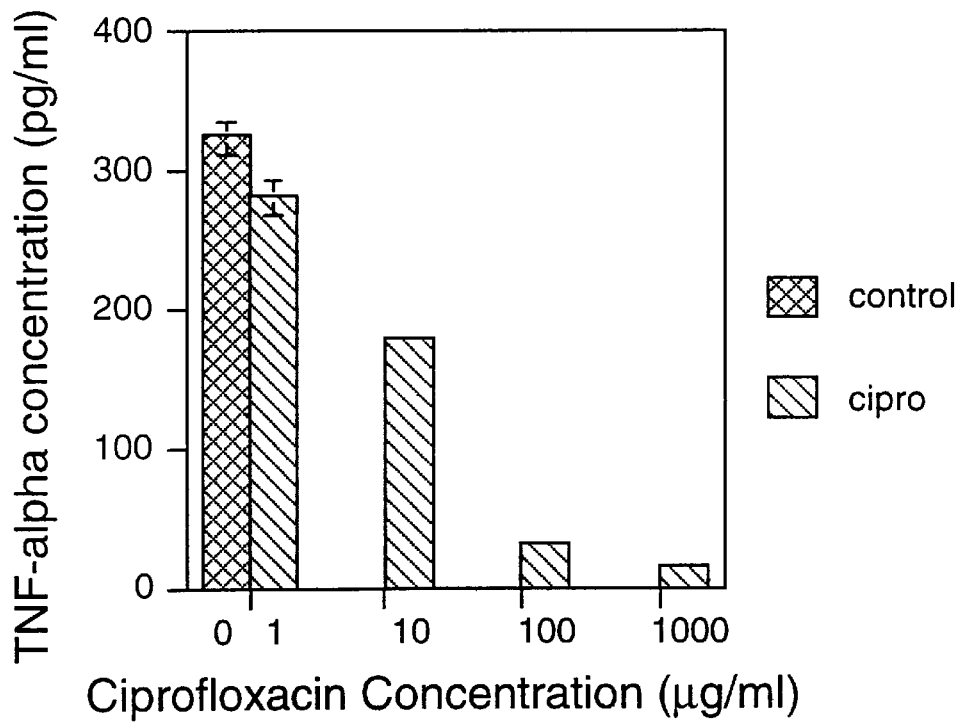
FIG. 3 is a bar graph illustrating the effect of ciprofloxacin on TNF-α release by peripheral blood monocytes.
Figure 4:
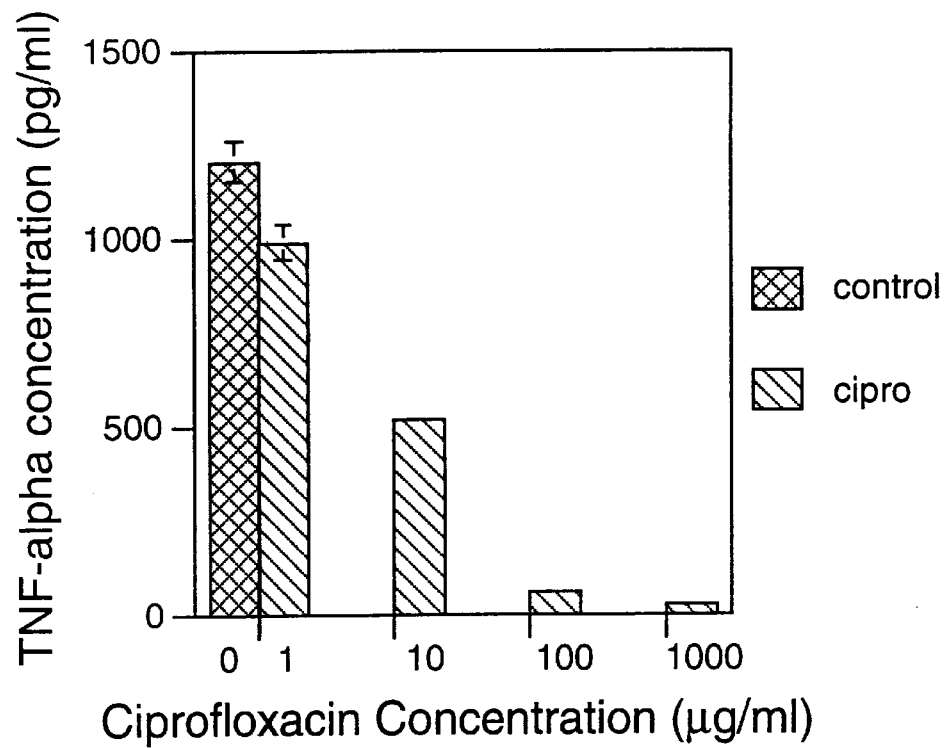
FIG. 4 is a bar graph illustrating the effect of ciprofloxacin on IL6 release by peripheral blood monocytes.

Peripheral blood monocytes were stimulated with titanium particles (Ti) or polymethylmethacrylate particles (pmma). Separate tests were conducted with isobutylmethyl xanthine $1\times10^{-3}$ M (IBMX), pentoxifylline $1\times10^{-4}$ M (PTX) and ciprofloxacin $1\times10^{-4}$ M (Cipro). The phosphodiesterase inhibitors all increased cyclic AMP and all decreased TNF-$\alpha$ release by peripheral blood monocytes. Ciprofloxacin has the additional effect of decreasing IL6 release. Ciprofloxacin causes a dose-dependent decrease in TNF-$\alpha$ and IL6 secretion by peripheral blood monocytes. The data resulting from these tests are shown in the bar graphs of FIGS. 1–4.

Although the invention has been described with respect to particular materials and methods as described above, the invention is only to be limited insofar as is set forth in the accompanying claims.

We claim:

1. A method of inhibiting cytokine-mediated bone resorption in a human patient comprising:

administering to said patient a therapeutic composition of matter constituent containing at least one pharamceutically acceptable, and a cytokine-mediated bone resorption inhibiting active agent in an amount effective to treat cytokine-mediated bone resorption in a patient for whom bone resorption treatment or prevention is indicated, wherein said cytokine-mediated bone resorption inhibiting active agent is selected from the group consisting of ciprofloxacin, pentoxifylline, isobutylmethyl xanthine, rolipram, and terferol.

2. The method according to claim 1 wherein said cytokine-mediated bone resorption inhibiting active agent is coated onto said constituent.

3. The method according to claim 1 wherein said cytokine-mediated bone resorption inhibiting active agent is incorporated in said article by means of a controlled release matrix containing said active agent.

4. The method according to claim 3 wherein said controlled release matrix containing said active agent includes capsules therein.

5. The method according to claim 3 wherein said controlled release matrix containing said active agent includes microcapsules therein.

6. A therapeutic composition of matter comprising:

an article selected from the group consisting of a bone cement constituent and an orthopaedic prosthesis constituent; and a cytokine-mediated bone resorption inhibiting active agent incorporated into said article in an amount effective to treat cytokine-mediated bone resorption in a patient for whom bone resorption treatment or prevention is indicated; and wherein said active agent is selected from the group consisting of pentoxifylline, isobutylmethyl xanthine, rolipram, and terferol.

7. The therapeutic composition according to claim 6 wherein said active agent is present in said article in an amount from about 0.001 to about 0.1 weight percent.

8. A therapeutic composition of matter comprising:

an article selected from the group consisting of a bone cement constituent and an orthopaedic prosthesis constituent; and a cytokine-mediated bone resorption inhibiting active agent incorporated into said article in an amount effective to treat cytokine-mediated bone resorption in a patient for whom bone resorption treatment or prevention is indicated; and wherein said active agent is ciprofloxacin which is present in said article in an amount from about 0.001 to about 0.1 weight percent.

* * * * *

UNITED STATES PATENT AND TRADEMARK OFFICE
CERTIFICATE OF CORRECTION

PATENT NO. : 6,010,711
DATED : January 4, 2000
INVENTOR(S) : Regis J. O'Keefe et al.

It is certified that error appears in the above-identified patent and that said Letters Patent is hereby corrected as shown below:

Column 4 Line 55, Claim 1, before "constituent" insert
--containing at least one pharmaceutically acceptable--.

Column 4 Lines 55, Claim 1, after "constituent" delete
--containing at least one pharmaceutically acceptable--.

Column 4 Lines 55-56, Claim 1, "pharamceutically" should read
--pharmaceutically--.

Column 5 Line 3, Claim 3, delete "article" and insert
--constituent--.

Signed and Sealed this

Fourteenth Day of November, 2000

Attest:

Q. TODD DICKINSON

*Attesting Officer*  *Director of Patents and Trademarks*